United States Patent
Kern (10) Patent No.: US 10,806,869 B2
(45) Date of Patent: Oct. 20, 2020

(54) DOSAGE INHALER

(71) Applicant: United Therapeutics Corporation, Silver Spring, MD (US)

(72) Inventor: Joachim Kern, Elsenfeld (DE)

(73) Assignee: UNITED THERAPEUTICS CORPORATION, Silver Spring, MD (US)

( * ) Notice: Subject to any disclaimer, the term of this patent is extended or adjusted under 35 U.S.C. 154(b) by 843 days.

(21) Appl. No.: 14/876,394

(22) Filed: Oct. 6, 2015

(65) Prior Publication Data

US 2016/0256637 A1 Sep. 8, 2016

Related U.S. Application Data

(63) Continuation of application No. 12/303,877, filed as application No. PCT/DE2007/001001 on Jun. 6, 2007, now Pat. No. 9,155,846.

(30) Foreign Application Priority Data

Jun. 7, 2006 (DE) .................... 10 2006 026 786

(51) Int. Cl.
*A61M 11/00* (2006.01)
*A61M 15/00* (2006.01)
(Continued)

(52) U.S. Cl.
CPC ......... *A61M 11/006* (2014.02); *A61M 11/002* (2014.02); *A61M 11/003* (2014.02);
(Continued)

(58) Field of Classification Search
CPC .. A61M 11/00; A61M 11/001; A61M 11/003; A61M 11/005; A61M 11/006;
(Continued)

(56) References Cited

U.S. PATENT DOCUMENTS 4,001,650 A 1/1977 Roman
4,007,238 A * 2/1977 Glenn .................... A61M 11/06
261/78.2
(Continued)

FOREIGN PATENT DOCUMENTS

AU 1999959533 B2 2/2000
DE 19838711 C1 6/2000
(Continued)

OTHER PUBLICATIONS

Abe et al., "Effects of inhaled prostacyclin analogue on chronic hypoxic pulmonary hypertension," J. Cardiovascular Pharmacology, 2001, 37, 239 251.
(Continued)

*Primary Examiner* — Colin W Stuart
*Assistant Examiner* — Douglas Y Sul
(74) *Attorney, Agent, or Firm* — Foley & Lardner LLP (57) ABSTRACT

A dosage inhaler includes an active liquid container, which contains a liquid having an active ingredient dissolved therein, and an atomizer by which the liquid is transformed into an aerosol and can be introduced into an aerosol dome, in which there is a baffle plate and to which an inlet tube and an outlet tube are attached, and an electronic control. The atomizer can be intermittently operated by a user and the user command readout is visible to the user. The generation of the amount of aerosol inside, and below, the aerosol dome is able to be separated in time from its eventual inhalation by (51) Int. Cl.
*A61M 16/06* (2006.01)
*A61M 16/00* (2006.01)

(52) U.S. Cl.
CPC ...... *A61M 11/005* (2013.01); *A61M 15/0018* (2014.02); *A61M 15/0021* (2014.02); *A61M 15/0065* (2013.01); *A61M 15/0085* (2013.01); *A61M 15/0086* (2013.01); *A61M 15/0096* (2014.02); *A61M 16/06* (2013.01); *A61M 16/0093* (2014.02); *A61M 16/0666* (2013.01); *A61M 2016/0024* (2013.01); *A61M 2016/0036* (2013.01); *A61M 2205/3313* (2013.01); *A61M 2205/3379* (2013.01); *A61M 2205/502* (2013.01); *A61M 2205/581* (2013.01); *A61M 2205/582* (2013.01); *A61M 2205/583* (2013.01); *A61M 2205/587* (2013.01); *A61M 2205/75* (2013.01)

(58) Field of Classification Search
CPC .......... A61M 11/0065; A61M 11/0085; A61M 11/0086
USPC ........ 239/338, 340, 343, 346, 370, 499, 504
See application file for complete search history.

(56) References Cited

U.S. PATENT DOCUMENTS

| | | | |
|---|---|---|---|
| 4,281,113 A | | 7/1981 | Axen et al. |
| 4,306,075 A | | 12/1981 | Aristoff |
| 4,306,076 A | | 12/1981 | Nelson |
| 4,349,689 A | | 9/1982 | Aristoff |
| 4,486,598 A | | 12/1984 | Aristoff |
| 4,635,647 A | * | 1/1987 | Choksi ................. A61B 5/0875 482/13 |
| 4,668,814 A | | 5/1987 | Aristoff |
| 4,677,975 A | * | 7/1987 | Edgar .................... A61M 15/00 128/200.14 |
| 4,683,330 A | | 7/1987 | Aristoff |
| 4,692,464 A | | 9/1987 | Skuballa et al. |
| 4,708,963 A | | 11/1987 | Skuballa et al. |
| 5,153,222 A | | 10/1992 | Tadepalli et al. |
| 5,234,953 A | | 8/1993 | Crow et al. |
| 5,361,989 A | * | 11/1994 | Merchat ............... A61M 11/005 239/102.2 |
| 5,497,763 A | | 3/1996 | Lloyd et al. |
| 5,865,171 A | * | 2/1999 | Cinquin ............... A61M 11/005 128/200.14 |
| 6,054,486 A | | 4/2000 | Crow et al. |
| 6,123,068 A | | 9/2000 | Lloyd et al. |
| 6,357,671 B1 | | 3/2002 | Cewers |
| 6,521,212 B1 | | 2/2003 | Cloutier et al. |
| 6,756,033 B2 | | 6/2004 | Cloutier et al. |
| 6,765,117 B2 | | 7/2004 | Moriarty et al. |
| 6,803,386 B2 | | 10/2004 | Shorr et al. |
| 6,809,223 B2 | | 10/2004 | Moriarty et al. |
| 7,199,157 B2 | | 4/2007 | Wade et al. |
| 7,261,102 B2 | * | 8/2007 | Barney ............. A61M 15/0028 128/200.14 |
| 7,384,978 B2 | | 6/2008 | Phares et al. |
| 7,417,070 B2 | | 8/2008 | Phares et al. |
| 7,544,713 B2 | | 6/2009 | Phares et al. |
| 9,155,846 B2 | * | 10/2015 | Kern .................... A61M 11/005 |
| 2003/0192532 A1 | | 10/2003 | Hopkins |
| 2004/0063912 A1 | | 4/2004 | Blumberg et al. |
| 2004/0105819 A1 | | 6/2004 | Hale et al. |
| 2004/0265238 A1 | | 12/2004 | Chaudry |
| 2005/0165111 A1 | | 7/2005 | Wade et al. |
| 2005/0183719 A1 | | 8/2005 | Wuttke et al. |
| 2005/0282901 A1 | | 12/2005 | Phares et al. |
| 2006/0147520 A1 | | 7/2006 | Ruegg |
| 2008/0200449 A1 | | 8/2008 | Olschewski et al. |
| 2008/0280986 A1 | | 11/2008 | Wade et al. |
| 2009/0036465 A1 | | 2/2009 | Roscigno et al. |
| 2010/0076083 A1 | | 3/2010 | Olschewski et al. |
| 2010/0282622 A1 | | 11/2010 | Phares |
| 2012/0177693 A1 | | 7/2012 | Cipolla et al. |
| 2012/0216801 A1 | | 8/2012 | Olschewski et al. |

FOREIGN PATENT DOCUMENTS

| | | | | |
|---|---|---|---|---|
| DE | 199 34 582 A1 | | 1/2001 | |
| DE | 19934582 A1 | * | 1/2001 | .......... A61M 11/005 |
| DE | 19938000 A1 | | 2/2001 | |
| DE | 10102526 A1 | | 7/2002 | |
| FR | 2783431 A1 | | 3/2000 | |
| JP | 2003-522003 A | | 7/2003 | |
| WO | WO 01/58514 A1 | | 8/2001 | |
| WO | WO 01/85241 A1 | | 11/2001 | |
| WO | WO-2007/134292 A2 | | 11/2007 | |

OTHER PUBLICATIONS

Agnew JE, Bateman RM, Pavia D, Clarke SW. (1984) Radionuclide demonstration of ventilatory abnormalities in mild asthma. Clinical Science; 66: 525-531.

Annals of the International Commission on Radiological Protection (ICRP) vol. 28, No. 3, 1998, Publication 80, Radiation Dose to Patients from Radiopharmaceuticals.

Aradigm Corporation news release Oct. 24, 2005, "Aradigm and United Therapeutics Sign Development and Commercialization Agreement Targeting Pulmonary Hypertension," Red Orbit News, http://www.redorbit.com/modules/news/tools.php?tool=print&id=281787, 2 pages.

Aristoff et al., "Synthesis of benzopyran prostaglandins, potent stable prostacyclin analogs, via an intermolecular mitsunobu reaction," Tetrahedron Letters, 1984, 25(36):3955-3958.

Bein et al., "Cardiovascular and pulmonary effects of aerosolized prostacyclin administration in severe respiratory failure using a ventilator nebulization system," J. Cardiovascular Pharmacology, 1996, 27, 583-586.

Benedict et al., "Evidence-based pharmacologic management of pulmonary arterial hypertension," Clinical Therapeutics, 2007, 29, 2134-2153.

Bindl et al., "Aerosolised prostacyclin for pulmonary hypertension in neonates," Archives of disease in childhood, Fetal and neonatal edition, 1994, 71(3), F214-6.

Blanchard, J.D., Cipolla, D., Liu, K., Morishige, R., Mudumba, S., Thipphawong, J., Taylor, G., Warren, S., Radhakrishnan, R., Van Vlasselaer, R., Visor , G. and Starko, K. (2003) Lung Deposition of Interferon Gamma-1b following Inhalation via AERx® System vs. Respirgard II™ Nebulizer Proc. ATS Annual Meeting (Abstract A373), Seattle.

Booke et al., "Prostaglandins in Patients with Pulmonary Hypertension: The Route of Administration," Anesth. Analg., 1998, 86:917, Letter to the Editor.

Boyd, B., Noymer, P., Liu, K., Okikawa, J., Hasegawa, D., Warren, S., Taylor, G., Ferguson, E., Schuster, J., Farr, S., and Gonda, I. (2004) Effect of Gender and Device Mouthpiece Shape on Bolus Insulin Aerosol Delivery Using the AERx Pulmonary Delivery System. Pharmaceutical Research. 21 (10) 1776-1782.

Byron, Peter R. "Drug Delivery Devices, Issues in Drug Development," Proc. Am. Thorac. Soc., 2004, 1:321-328.

Channick et al., "Safety and efficacy of inhaled treprostinil as add-on therapy to bosentan in pulmonary arterial hypertension," J. American College of Cardiology, 2006, 48, 1433-1437.

Colthorpe P, Taylor G, Farr SJ. (1997) A comparison of two non-invasive methods for quantifying aerosol deposition in the lungs of rabbits. J. Aerosol Med.; 10:255.

Doyle et al., "Inhaled prostacyclin as a selective pulmonary vasodilator," Anaesthesia and Intensive Care, Aug. 1996, 24(4):514-515.

Dumas et al,. "Hypoxic pulmonary vasoconstriction," General Pharmacology, 1999, 33, 289-297.

Dworetz et al., "Survival of infants with persistent pulmonary hypertension without extracorporeal membrane oxygenation," Pediatrics, 1989, 84, 1-6.

(56) References Cited

OTHER PUBLICATIONS

EPA Integrated Risk Information System (IRIS): data sheet for 3-methylphenol (m-cresol). Accessed at http://www.epa.gov/iris/subst/0301/htm on Mar. 9, 2014.
Ewert et al., "Aerosolized iloprost for primary pulmonary hypertension," New England Journal of Medicine, 2000, 343, 1421-1422.
Ewert et al., "Iloprost als inhalative bzw. Intravenose langzeitbehandlung von patienten mit primarer pulmonaler hypertonie," Z. Kardiol., 2000, 89, 987-999, English summary on first page.
Farr et al., "Comparison of in vitro and in vivo efficiencies of a novel unit-dose liquid aerosol generator and a pressurized metered dose inhaler," International Journal of Pharmaceutics, 2000, 198:63-70.
Findlay et al., "Radioimmunoassay for the Chemical Stable Prostacyclin Analog, 15AU81: a Preliminary Pharmacokinetics Study in the Dog," Prostaglandins Leukot. Essent. Fatty Acids, Feb. 1993, 48(2):167-174.
Fink et al., "Use of Prostacyclin and its Analogues in the Treatment of Cardiovascular Disease," Heart Disease, 1999, 1:29-40.
Gessler et al., "Ultrasonic versus jet nebulization of iloprost in severe pulmonary hypertension," Eur. Respir. J., 2001, 17, 14-19.
Ghofrani et al., "Hypoxia- and non-hypoxia-related pulmonary hypertension—Established and new therapies," Cardiovascular Research, 2006, 72:30-40.
Haraldsson et al., "Comparison of inhaled nitric oxide and inhaled aerosolized prostacyclin in the evaluation of heart transplant candidates with elevated pulmonary vascular resistance," Chest, 1998, 114, 780-786.
Hoeper et al., "A comparison of the acute hemodynamic effects of inhaled nitric oxide and aerosolized iloprost in primary hypertension," J. American College of Cardiology, 2000, 35, 176-182.
Hoeper et al., "Effects of inhaled nitric oxide and aerosolized iloprost in pulmonary veno-occlusive disease," Respiratory Medicine, 1999, 93, 62-70.
Hoeper et al., "Long term treatment of primary pulmonary hypertension with aerosolized iloprost, a prostacyclin analogue," New England Journal of Medicine, 2000, 342, 1866-1870.
Howarth, P.H., "Why particle size should affect clinical response to inhaled therapy," Journal of Aerosol Medicine, 2001, 14 Supp. 1, S-27-S-34.
Ichida et al., "Additive effects of beraprost on pulmonary vasodilation by inhaled nitric oxide in children with pulmonary hypertension," American Journal of Cardiology, 1997, 80, 662-664.
Krause et al., "Pharmacokinetics and pharmacodynamics of the prostacyclin analogue iloprost in man," Eur. J. Clin. Pharmacol., 1986, 30, 61-68.
Lee et al., "Current strategies for pulmonary arterial hypertension," J. Internal Medicine, 2005, 258, 199-215.
Martin, John C., "Inhaled Form of Remodulin in the Pipeline," http://www.phneighborhood.com/content/in_the_news/archive_2320,aspx, ph Neighborhood, Oct. 28, 2005, 2 pages.
Max et al., "Inhaled prostacyclin in the treatment of pulmonary hypertension," Eur. J. Pediatr., 1999, 158 Suppl 1, S23-S26.
McNulty et al., "The Pharmacokinetics and Pharmacodynamics of the Prostacyclin Analog 15AU81 in the Anesthetized Beagle Dog," Prostaglandins Leukot. Essent. Fatty Acids, Feb. 1993, 48(2):159-166.
Miller et al., "Standardisation of spirometry. Series ATS/ERS Task Force: Standardisation of Lung Function Testing" Eur Respir J 2005; 26: 319-338.
National Radiological Protection Board. Doses to Patients from Medical Radiological Examinations in Great Britain. (1986) Radiological Protection Bulletin No. 77.
Nebu-Tec med. Produkte Eike Kern GmbH, VENTA-NEB®-ir A-I-C-® Operating Instrutions, Sep. 2005.
Notes for Guidance on the Clinical Administration of Radiopharmaceuticals and Use of Sealed Radioactive Sources. Administration of Radioactive Substances Advisory Committee (ARSAC) (Mar. 2006). ARSAC Secretariat, Chilton, Didcot, Oxon. OX11 0RQ.
Olschewski et al. for the German PPH Study Group, "Inhaled iloprost to treat severe pulmonary hypertension—An uncontrolled trial," Annals of Internal Medicine, 2000, 132, 435-443.
Olschewski et al., Aerosolized prostacyclin and iloprost in severe pulmonary hypertension,: Annals of Internal Medicine, 1996, 124, 820 824.
Olschewski et al., "Inhaled prostacyclin and iloprost in severe pulmonary hypertension secondary to lung fibrosis," Am. Respir. Crit. Care Med., 1999, 160, 600-607.
Olschewski et al., "Pharmacodynamics and pharmacokinetics of inhaled iloprost, aerosolized by three different devices, in severe pulmonary hypertension," Chest, 2003, 124, 1294-1304.
Olschewski et al., "Prostacyclin and its analogues in the treatment of pulmonary hypertension," Pharmacology and Therapeutics, 2004, 102, 139-153.
Olschewski et al., "Recovery from circulatory shock in severe primary pulmonary hypertension (PPH) with aerosolization of iloprost," Intensive Care Med., 1998, 24, 631-634.
Pappert et al., "Aerosolized Prostacyclin Versus Inhaled Nitric Oxide in Children with Severe Acute Respiratory Distress Syndrome," Anesthesiology, Jun. 1995, 82(6):1507-1511.
Publications of the International Commission on Radiological Protection (ICRP) (1977) Recommendations of the International Commission on Radiological Protection 26.
Pulmonary Delivery, ONdrugDelivery, 2006, 5 pages.
Rigby, Jonathan, Aradigm Corporation, "Technological advances for success: Product pipeline in targeted pulmonary delivery," Pulmonary Delivery Innovative Technologies Breathing New Life into Inhalable Therapeutics, ONdrugDelivery, http://www.ondrugdelivery.com/publications/Pulmonary.pdf, 2006, 17-19.
Saini et al., "Effect of Electrostatic Charge and Size Distributions on Respirable Aerosol Deposition in Lung Model," Industry Applications Conference, 2004, $39^{th}$ IAS Annual Meeting, Conference Record of the 2004 IEEE Seattle, WA, Oct. 3-7, 2004, 2:948-952.
Sandifer et al., "Potent effects of aerosol compared with intravenous treprostinil on the pulmonary circulation," J. Appl. Physiol., 2005, 99:2363-2368.
Santak et al., "Prostacyclin aerosol in an infant with pulmonary hypertension," Eur. J. Pediatr., 1995, 154, 233-235.
Soditt et al., "Improvement of oxygenation induced by aerosolized prostacyclin in a preterm infant with persistent pulmonary hypertension of the newborn," Intensive Care Med., 1997, 23, 1275-1278.
Steffen et al., "The Effects of 15AU81, a Chemically Stable Prostacyclin Analog, on the Cardiovascular and Renin-Angiotensis Systems of Anesthetized Dogs," Prostaglandins, Leukotrienes and Essential Fatty Acids, 1991, 43:277-286.
Stricker et al., "Sustained improvement of performance and haemodynamics with long-term aerosolized prostacyclin therapy in severe pulmonary hypertension," Schweiz Med. Wochenschr., 1999, 129, 923-927.
Van Heerden et al., "Inhaled aerosolized prostacyclin as a selective pulmonary vasodilator for the treatment of severe hypertension," Anaesthesia and Intensive Care, 1996, 24, 87-90.
Van Heerden et al., "Re: Delivery of inhaled aerosolized prostacyclin (IAP)," Anaesthesia and Intensive Care, 1996, 24, 624-625.
Voswinckel et al., "Acute effects of the combination of sildenafil and inhaled treprostinil on haemodynamics and gas exchange in pulmonary hypertension," Pulmonary Pharmacology & Therapeutics, 2008, 21, 824-832.
Voswinckel et al., "Favorable Effects of Inhaled Treprostinil in Severe Pulmonary Hypertension: Results from Randomized Controlled Pilot Studies" J. Am. Coll. Cardiol., 48(8):1672-1681 (2006).
Voswinckel et al., "Inhaled Treprostinil for Treatment of Chronic Pulmonary Arterial Hypertension," Annals of Internal Medicine, Jan. 17, 2006, 144(2):149-150.
Walmrath et al., "Effects of inhaled versus intravenous vasodilators in experimental pulmonary hypertension," Eur. Respir. J., 1997, 10, 1084-1092.
Wasserman et al., "Bronchodilator effects of prostacyclin (PGI2) in dogs and guinea pigs," European Journal of Pharmacology, 1980, 66, 53-63.

(56) References Cited

OTHER PUBLICATIONS

Webb et al., "The use of inhaled aerosolized prostacyclin (IAP) in the treatment of pulmonary hypertension secondary to pulmonary embolism," Intensive Care Med., 1996, 22, 353-355.

Wensel et al., "Effects of iloprost inhalation on exercise capacity and ventilator efficiency in patients with primary pulmonary hypertension," Circulation, 2000, 101, 2388-2392.

Wetzel, R.C., "Aerosolized prostacyclin: in search of the ideal pulmonary vasodilator," Anesthesiology, 1995, 82, 1315-1317.

Wittwer et al., "Inhalative Pre-Treatment of Donor Lungs Using the Aerosolized Prostacyclin Analog Iloprost Ameliorates Reperfusion Injury," J. Heart Lung Transplant, 2005, 24:1673-1679.

Zanen et al., "Optimal particle size for beta 2 agonist and anticholinergic aerosols in patients with severe airflow obstruction," Thorax, 1996, 51, 977-980.

Zanen et al., "The optimal particle size for β-adrenergic aerosols in mild asthmatics," International Journal of Pharmaceutics, 1994, 107, 211-217.

Non-Final Office Action dated Jan. 29, 2015 in U.S. Appl. No. 13/120,015.
Final Office Action dated Jul. 2, 2013 in U.S. Appl. No. 13/120,015.
Non-Final Office Action dated Oct. 31, 2012 in U.S. Appl. No. 13/120,015.
Non-Final Office Action dated Mar. 13, 2015 in U.S. Appl. No. 13/469,854.
Final Office Action dated Mar. 13, 2014 in U.S. Appl. No. 13/469,854.
Non-Final Office Action dated Oct. 3, 2012 in U.S. Appl. No. 13/469,854.
Final Office Action dated Oct. 10, 2014 in U.S. Appl. No. 12/591,200.
Non-Final Office Action dated Mar. 9, 2014 in U.S. Appl. No. 12/591,200.
Final Office Action dated Oct. 17, 2012 in U.S. Appl. No. 12/591,200.
Final Office Action dated Dec. 22, 2011 in U.S. Appl. No. 12/591,200.
Office Action dated Dec. 1, 2015, in corresponding Korean Application No. 10-2011-7008976, and English translation, 6 pages.

* cited by examiner

DOSAGE INHALER

CROSS-REFERENCE TO RELATED APPLICATIONS

The present application is a continuation of U.S. patent application Ser. No. 12/303,877 filed Jan. 5, 2009, which is the U.S. national Stage of PCT/DE2007/001001 filed Jun. 6, 2007 which claims priority from German Patent Application No. 102006026786.9 filed Jun. 7, 2006, all of which are incorporated herein by reference in their entireties.

The invention relates to a dosing inhaler, consisting of an active liquid container, which contains a liquid having an active substance dissolved therein, and an atomizer, by means of which the liquid can be transformed into an aerosol and introduced into an aerosol dome, in which a baffle plate is arranged, and to which a supply-air tube and an exhaust-air tube are connected, and an electronic control.

The inhalation of active substances that are dissolved in water and inhaled as a fine mist has long been well known as a method of administering active substances, particularly in the medical field. The finer the droplets, the greater is the proportion that is transported deep into the lung with the respiratory air. In the prior art, a mist is generated by means of an ultrasonic oscillator. It is either arranged on the base of the vessel with the active liquid, and generates on the surface of said liquid a spray that isolates a mist so fine that it behaves as smoke and can therefore be easily entrained with the air stream. It is necessary that, to separate out aerosol droplets larger than about 10 microns, the air stream must be diverted at least twice. To this end, a baffle plate is arranged above the ultrasonic spray. A downwardly open, hollow truncated cone has been found most effective. The droplets rise into this truncated cone and are set into turbulence in the centre of the cone, the larger drops being removed from the mist and falling backing into the active liquid container. Only the very finest drops are entrained with the air stream and transported around the edge of the baffle either via a narrow slit or through calibrated openings into the exhaust air channel. At this point, further undesirably large droplets are separated out.

Particularly efficient is the principle of active substance transport into the lung by means of an aerosol, as a result of the very small droplets that are possible with ultrasonic atomizers. It can be proven that droplets below a minimum size are completely absorbed into the lung sacs and transferred to the blood.

However, a severe weakness is the exact dosage of the active substance. Though it is also a principal advantage of inhalation that, in comparison to all other methods of administration of drugs, very small amounts, in absolute terms, are required, it is primarily only a psychological problem that, of the active liquid, a residue of the order of single-digit percentages remains in the active substance container. If the amount falls below this minimum quantity, the ultrasonic oscillation no longer generates a spray and also does not form water droplets any longer.

However, this minimum amount can be calculated in advance with good accuracy and therefore only the dosage to be administered can be added.

With the exact dosage of the active substance amount actually absorbed by the patient, according to the prior art, the most serious problem is the patient's respiratory behaviour, which can be neither monitored nor controlled with the equipment known in the prior art. Unlike oral administration—in which an unwilling and/or debilitated and/or unconcentrated patient either takes the medication dose completely, or doesn't take it at all, however it is only in a practically negligible number of cases that he accidentally takes a partial dose—with the inhalers of the prior art, it is very often the case that only a part of the active substance dose transformed into the aerosol is actually taken by the patient. The rest is either transformed from the aerosol state back into a liquid, or, because of insufficient air velocity, is deposited in the tube systems of the inhaler or only passes as far as the patient's mouth/throat area. In simple devices without supply air and respiratory valve, it can also occur that the patient does not inhale the aerosol, but also blows it out of the device into the environment.

On this basis, it is the object of the invention to develop a dosing inhaler in which the patient receives clear and unmistakable instructions about how he must breath, these commands not only being communicated via text but also by means of other optical elements and/or acoustic signals, and in which it is monitored whether the patient is breathing at all and, if so, in which direction, and in which it is additionally checked whether an aerosol is present or not. The main object is that the device produces a precisely dosed amount of aerosol, the production of which can be separated in time from the process of inhalation, and the whereabouts of which can be checked.

As a solution, the invention proposes a dosing inhaler in which the atomizer can be intermittently operated and a user command output is noticeable for the user, and the generation of the aerosol volume within and below the aerosol dome can be separated in time from the inhalation thereof.

Form the point of view of the physical principle of action, the wholly decisive distinction of the invention from the inhalation devices of the prior art is that the atomizer is only briefly operated. A precise dosage is achieved in that, at normal room temperature and in the known volume of the aerosol dome, with interior air that is proven in advance to be aerosol-free, independently of the precise operating time of the atomizer through physical saturation of the interior air, a completely determined aerosol volume with high, reproducible accuracy is produced in each operating cycle. For the accuracy, it is thus not the operating time of the atomizer that is important, but the fact that the interior air is aerosol-free at the beginning of each new cycle and in that, during aerosol production, the atomizer is operated until the state of saturation has been reliably achieved.

The production of the precisely dosed aerosol amount is thus ensured according to the state of the art.

After production is complete, it must then be monitored that the aerosol disappears completely from the interior chamber below the aerosol dome until the next production cycle.

The basic concept of the invention is to ensure that this dose of the active substance also passes completely into the alveolae. To this end, the dosing inhaler according to the invention is served by a user-command output, which is recognizable to the user of the device in every operating state. This command output, like the atomizer, is controlled via the electronic control, so that the chronologically correct sequence is ensured.

As an alternative embodiment for the production of the aerosol, a carrier liquid container can be arranged between the active fluid container and the atomizer. In this variant, the active liquid container is preferably conical in design. The active liquid is filled into the truncated cone standing on its (rounded) tip. The rounded tip of the cone dips into the carrier liquid, which is energized, by the ultrasonic oscillator, into oscillations, which are transmitted via the wall of the active fluid container to the active liquid. The carrier liquid thus serves as a coupling for high-frequency oscillations. The decisive advantage of this arrangement is that the active liquid is only dissipated in a very small range of the device, and therefore the risk of contamination with undesirable substances is reduced.

It has proven useful to use the lower part of the active fluid container, which is made of a thin and oscillation-capable polymer, only for a single inhalation operation and then to dispose of it. This makes it unnecessary to clean a container to be used repeatedly, which drastically reduces the risk of entraining undesirable bacteria into the lung.

To monitor for the presence of aerosol, the invention proposes installing a density sensor, which monitors the space above the active fluid container and below the aerosol dome. In its simplest embodiment, this density sensor is an infrared sensor, which can register—with a certain tolerance—the fact that the monitored space is either free of aerosols or is filled with an aerosol in the desired minimum concentration. This infrared sensor is evaluated by the electronic control and used for controlling the respiratory commands. In a sub-variant, it is conceivable that the density sensor not only registers the two states "aerosol free" and "aerosol present", but can also register intermediate values with a reproducible accuracy. In this sub-variant, it is appropriate that volumes of aerosol that have not been completely transported as a result of incorrect use, are indeed transported into the patient's lung through appropriately repeated respiratory commands. But also in its simplest embodiment, the density sensor, for the electronic control, is the crucial basis for monitoring the actual compliance with the respiratory command.

For the respiratory commands to the use, each dosage inhaler according to the invention is equipped with a user-command output. The most diverse variants for this interface according to the state of the art for human-machine interfaces can be realized. They include acoustic signals such as simple sounds, melodies or speech. Electromagnetic signal transducers, such as the vibrators, rotating electrical drives with an unbalanced weight, known from mobile phones.

However, the invention prefers optical signals. They include light-emitting diodes, incandescent bulbs and other self-illuminating elements, mechanically hinged signal areas with and without lighting, and, as a preferred element, a display, e.g. as an LCD (liquid crystal display). On such a display, illuminated symbols, other graphic representations and texts may be illuminated. In particular, English-language commands are preferred, since this language is the current global standard for electronic equipment, and because comparatively few characters are sufficient in this language.

Independently of the chosen form of user-command output, the invention, in the simplest version, proposes the following five commands. "Ausatmen", "Einatmen", "Warten", "Ende or "Falsch-nutzung". The comparison with the English translations: Exhale, Inhale, Wait, End, Fault, shows how few characters are required to transmit the commands.

Of course, however, all other types of lettering and conceivable symbolic representations that are known and conventional are suitable for a dosing inhaler according to the invention.

As an appropriate design, the invention proposes that an aerosol filter and a supply-air valve are arranged before the supply-air tube. The aerosol filter ensures that almost no aerosol escapes even in the time interval during which the supply-air valve has not yet been sealed. That is particularly necessary in the interests of precise metering. A further reason for installing a filter is that it also allows the inhalation of substances that, though they have a beneficial effect overall in small amounts, may be unpleasant or even potentially harmful in larger amounts for uninvolved persons.

As a further appropriate equipment, the invention quotes the invention of a respiration detector in the supply-air tube. It can distinguish whether an air-flow prevails at all in the supply-air tube and in which direction it flows. In the minimum configuration, the air volume is only monitored by means of a single threshold value, which the value falls either below or above. In a refined embodiment, the registering of intermediate values is also possible and appropriate.

As a further detail in the interest of an improved achievement of the object, it is also conceivable that the supply-air valve no longer requires, as a passive element, a particular minimum air flow in order to close but instead is actively closed and opened by the control by means of its own drive assigned to the supply-air valve.

According to the state of the art for inhalers, a dosage inhaler according to the invention can be extended at its exhaust-air tube with a mouthpiece, a nasal piece or a face mask. It is also conceivable—e.g. for bed-ridden patients—to insert a small extension tube there-between, so that the functional regions of the dosing inhaler remain in the preferred vertical orientation for any orientation of the patient's face. In this case, care should be taken that the user can still perceive the commands of the user-command output. An optical display must therefore not be covered or be out of the patient's field of view. Otherwise, a hinged display must be installed for these applications.

As a further comfort feature, a dosing inhaler according to the prior art can also be fitted with an exhalation tube that can be connected, e.g., to the aerosol dome.

The exhalation filter, corresponding to the supply-air tube, should also have an aerosol filter and an exhalation filter at the end.

The invention prefers that the exhalation tube is also connected to the respiration detector. It is conceivable that the valve in the exhalation tube also obtains its own drive, which can be activated by the electronic control. In a similar way to an externally driven valve in the supply-air tube, the valve is thereby also closed in the exhalation tube before an air stream occurs in a direction that—in this phase—is undesirable, so that an undesirable inlet and outlet of aerosol through the exhalation tube can be completely avoided.

The dosing inhaler according to the invention, which is equipped with all the additional extras described above, ensures the complete inhalation of each produced partial quantity of the aerosol in the first, active level of the control, through to the user-command output, which is actuated according to the cycle. For correct use of the dosing inhaler, the patient must then only charge it with the respectively prescribed active substances in the amount determined by the doctor, and ensure that the device is cleaned and provide with an adequate amount of carrier liquid.

After this preliminary work, it is sufficient to activate the dosing inhaler by means of a single, simple starting button. The dosing inhaler thereupon starts to produce aerosol and is meanwhile signalling "exhale" to the user. When the aerosol production is concluded, the electronic control switches off the atomizer and signals "inhale" to the user via the user-command output. As soon as the inhalation time is over, the dosing inhaler switches over to the "wait" phase, while the air stream in the interior subsides and large aerosol drops still in suspension fall back into the active fluid container. After this waiting time, a new exhalation phase begins during which the next aerosol production starts up. The next cycle thus commences.

As with all other MMI (man-machine interfaces), the user-command output of the dosing inhaler according to the invention depends on the user also actually following the issued commands. To facilitate this, they are—as described above—clearly and unambiguously formulated, and illuminate in a logical sequence. When the user follows these unambiguous commands, perfect functioning of each step is ensured. In practice, however, it is conceivable that the user may not execute the commands completely but as a result of poor concentration and/or weakness and/or dementia and/or for other reasons may follow them only partly, or not at all, or even do the opposite to what the user command output prescribes.

For these cases, a dosing inhaler according to the invention offers, as an additional feature, that in the second, passive level of the control, the presence of absence of an aerosol is monitored and the air direction and air amount is recognized both in the supply-air tube and in the exhalation tube. In addition, in this second monitoring plane, further connections and controls are possible, with which the functional reliability of the dosing inhaler is further improved even in the case of incorrect operation. It is thus appropriate, with the presence of a driven exhalation valve and/or supply-air valve, that the command symbol for "inhale" can only be issued after the opening of the supply-air valve and/or the closing of the driven exhalation valve. Correspondingly, the command for "exhalation" should only be issued after closing of the driven supply-air valve and/or the opening of the driven exhalation valve.

As described, each breathing cycle, with the use of a dosing inhaler according to the invention, consists of phase 1 "aerosol preparation", phase 2 "inhale" and phase 3 "wait". For even better monitoring of the actual observance of these commands to the user, further control connections of the electronic controls to the sensors and the user-command output are appropriate.

Thus, an additional assurance that, in the first phase, "aerosol preparation", the reaching of the desired aerosol amount by the density sensor is continually checked and if it is not reached, the atomizer is activated again, until the desired aerosol density is recognizable by the density sensor.

In a further refinement of the control, the number of possible attempts can be limited and an error report output after this number has been exceeded. Behind this is the idea that, in a normal case, the desired amount of aerosol has been produced and is present after a single oscillation cycle. If, even after multiple vain attempts, the density sensor still reports no amount of aerosol as present, either the atomizer is defective, the liquid is missing, or the density sensor is no longer functional.

As a further convenience detail in the actuation of the user-command output, the invention describes the problem that, although the command symbol for "exhale" is activated, the respiration detector on the exhalation tube is passive, which indicates that the patient is not observing the issued "exhale" command at that moment. As a response, the electronic control can intensify the command symbol for "exhale", e.g. by flashing the first display or activating a further command display, such as a speech output.

Corresponding to the aforesaid problem of omission of exhalation in the correct phase, the command for "inhale", as described above, can be amplified in the (important) inhalation phase if the respiration identification fails to arrive.

In the case of both command amplifications, the (amplified) signal can be switched off after the respectively provided maximum time. If, e.g., in the "inhalation" phase, the respiration detector on the supply-air tube is active only temporarily or not at all, and if the density sensor still reports the presence of aerosol, the electronic control should still switch over to the "exhale" command. If, after the end of the time provided for exhalation, the density sensor still reports the presence of aerosol, and if the maximum "lifetime" of an aerosol has still not been exceeded, the "inhale" command should be issued again so that the remaining residual aerosol amount is completely absorbed.

It is one of the significant advantages of the dosing inhaler according to the invention is that, if an inhalation does not take place, the electronic control does not classify the produced aerosol amount as already inhaled, but assumes that it has passed back into the active liquid container. Correspondingly, the electronic control will start at least one additional cycle to ensure that, at the end of the process, the desired dosage is still actually taken up by the patient.

The electronic control can thereby take into account that the aerosol is only stable for a limited time and then the droplets have either passed directly back into the active liquid container or have arrived there by condensing on the walls and running back into the container.

Further details and features of the invention are explained below in greater detail with reference to examples. However, they are not intended to limit the invention but only explain it. In schematic view.

In detail, the figures show.

Figure 1:
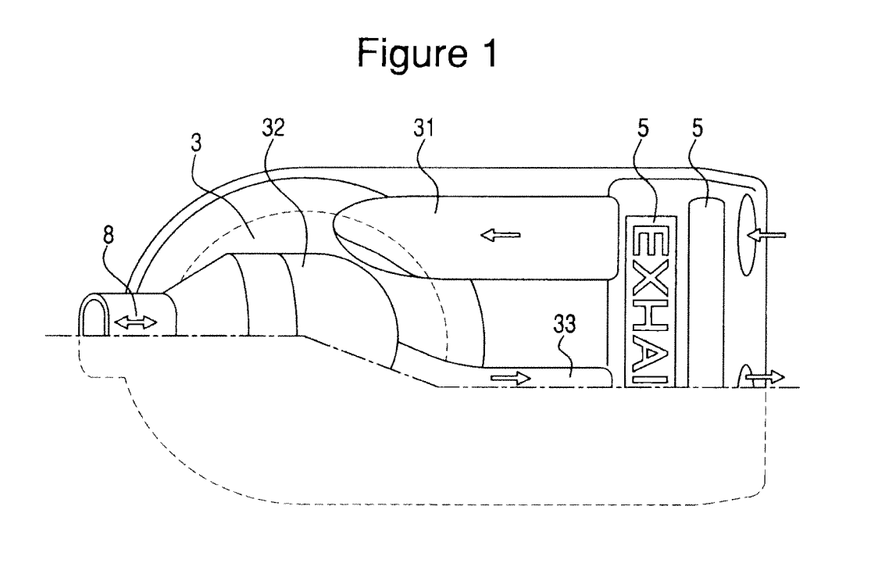
FIG. 1 shows an elevation of a dosing inhaler with two mutually offset sectional planes for FIGS. 2 and 3.

FIG. 1 shows the elevation of a dosing inhaler according to the invention. The left half shows the aerosol dome 3 with a dotted line. It is dotted because it is covered by the exhaust-air tube 32 and the cupola following it, which is arranged so as to be concentric to the aerosol dome 3.

The exhaust-air tube 32 is also arranged so as to be concentric to the aerosol dome 3. In the elevation of the device in FIG. 1, a mouthpiece 8 that emerges laterally from the exhaust-air tube 32 is visible at the left-hand side. In FIG. 1, it can be followed how inhaled air enters through the opening shown at the top right-hand side, enters the supply-air tube 31 below the user-command output 5, and from there passes via the aerosol dome 3 into the cupola. The air direction is marked by two arrows.

In the "exhale" state, the air in the mouthpiece 8 moves in the other direction, as marked by a double arrow. The exhaled air can then escape again through the exhalation tube 33. Only a part of the exhalation tube 33 is drawn; the rest is cut-off in the view. Likewise, only half of the mouthpiece 8 is represented. FIG. 1 shows the double-kinked section plane of FIGS. 2 and 3 with a dash-dotted line.

The silhouette of the complete unit is shown in the lower region of FIG. 1 with a dotted line.

Figure 2:
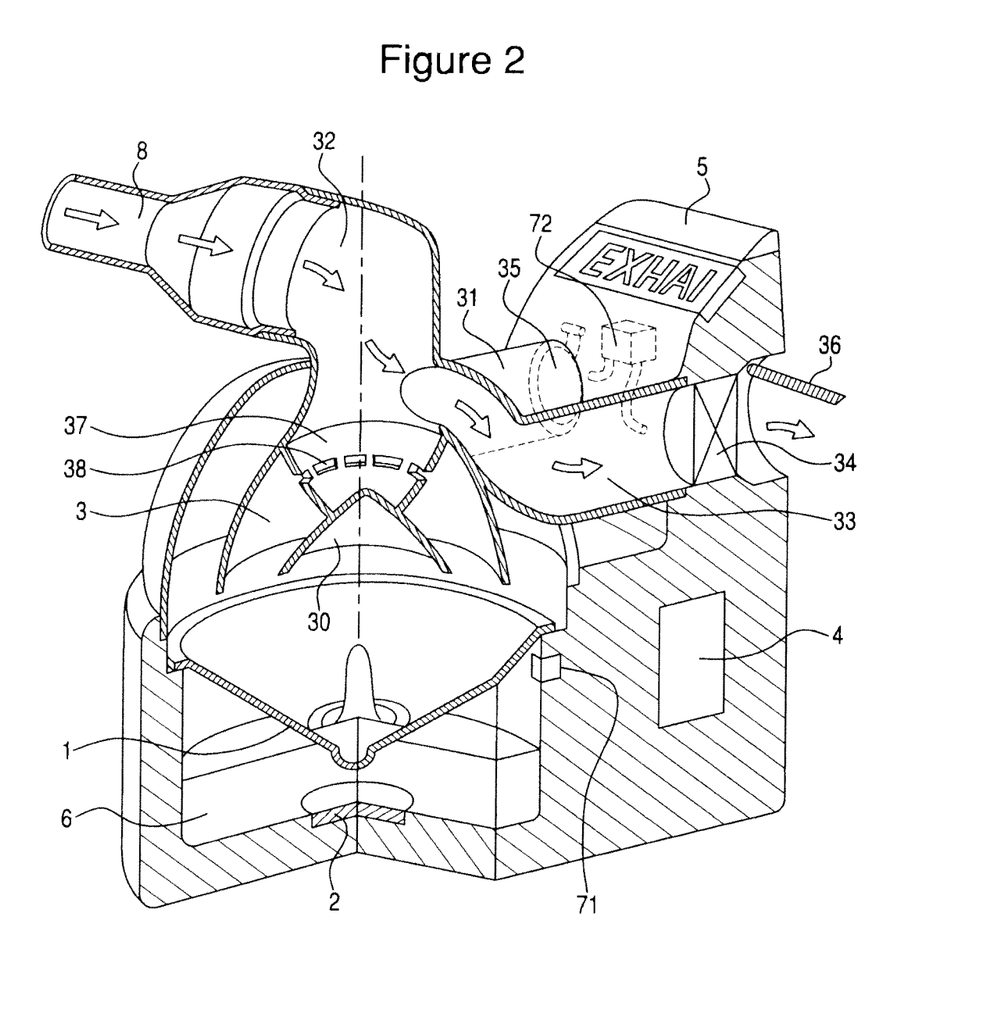
FIG. 2 shows a skew projection of a dosing inhaler with a section through the aerosol dome or receiver and exhalation tube in the "exhalation phase"

FIG. 2 shows the dosing inhaler shown in elevation in FIG. 1 as a skew projection, namely with a section in the doubly kinked sectional plane defined in FIG. 1. By this means it is possible to view the centre point of the active-fluid container 1 with the spray and also a section through the exhalation tube 33.

In FIG. 2, the atomizer 2, an ultrasonic oscillator, can be seen on the base of the carrier-liquid container 6. It is comprehensible how the oscillations of the atomizer 2 are transmitted to the active liquid via the carrier liquid in the carrier-liquid container 6 and via the—in this example conical—active-liquid container 1.

In FIG. 2, the first phase of the cycle is shown, namely the aerosol preparation. In this phase, the atomizer 2 oscillates and transmits the oscillations to the carrier liquid, and from there via the active fluid container to the active liquid itself. This forms the spray, which can be seen in FIG. 2 and separates out the aerosol clouds, which can be seen in FIG. 2 as dotted regions within the active liquid container 1.

During the aerosol preparation, the patient should exhale. That is ordered in the user-command output 5 by the command "exhale". In this phase, the patient must not release his mouth from the mouthpiece 8, but can breath normally, which is represented by the air stream characterized by the arrow. The air streams from the mouthpiece 8 into the exhaust-air tube 32 and from there via the slit 38 into the aerosol dome 3 and into the exhalation tube 33. The air passes through the aerosol filter 34, opens the exhalation valve 36 and then emerges into the ambient air. In FIG. 2, it can be seen how the exhalation air has opened the exhalation valve 36 by virtue of its flow.

In FIG. 2, it can be followed that, in the exhalation phase, no aerosol can emerge from the region below the aerosol dome 3, because the air pressure, which is somewhat elevated by exhalation, also continues into the supply-air tube 31, where it closes the supply-air valve 35, so only the route through the exhalation tube 33 remains.

In FIG. 2, the exhalation detector 72 is shown with a dotted line, which can be connected with a small tube to the exhalation tube 33. The exhalation detector 72 detects that air streams through the exhalation tube in this state.

In FIG. 2, it is made plausible that the density sensor 71, as an infrared sensor, can detect the presence of the aerosol clouds—shown here with a dotted line—through the wall of the active-liquid container 1.

Figure 3:
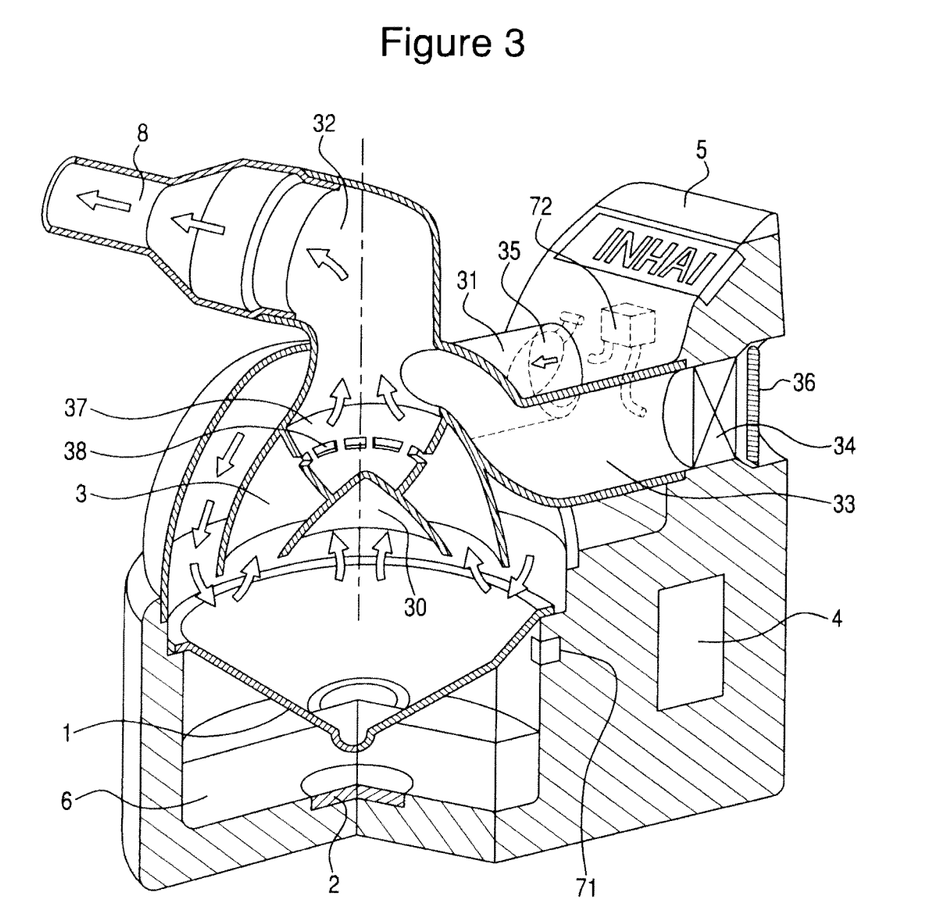
FIG. 3 shows a skew projection view of a dosing inhaler with a section through the aerosol dome or receiver and exhalation tube in the "inhalation" phase.

FIG. 3 shows the same section through a three-dimensionally-represented dosing inhaler, as in FIG. 2, but in the "inhale" state.

In FIG. 3, the aerosol clouds can now be seen within the truncated cone of the baffle 30. Two arrows indicate how the aerosol clouds swirl there.

Another arrow in the supply-air tube 31 shows the direction of the entering air. It can be seen that the supply-air valve 35 is open in the "inhale" state. The exhalation valve 36 located next to it is closed in this phase and pivots back into the unit.

In FIG. 3, the further course of the inhaled air can be followed:

From the supply-air tube 31, the air enters a cupola above the aerosol dome 3. Two arrows in the left-hand cutaway region of this cupola show the course of the air direction. The air then streams on towards the lower edge of the aerosol dome 3, where it enters the aerosol dome 3. In the process, it entrains the aerosol clouds, which are located below the baffle plate 30. The inhalation suction causes the aerosol clouds within the aerosol dome 3 to flow up again and pass through the slit 38 in the hollow-conical holder 37 into the exhaust-air tube 32. Here, the aerosol clouds—shown as dotted lines—are recognizable and flow into the mouthpiece 8, and from there into the patient's lung.

In FIG. 3, it is made clear that—in the illustrated end—part of the "inhale" phase of the density sensor 71 can no longer report the presence of aerosol in the active fluid container 1, since all the aerosol clouds have already found their way out of the active liquid container 1.

The electronic control 4 is only drawn schematically in FIGS. 2 and 3. The functional connection to the atomizer, to the density sensor 71 and to the respiration detector 72 are not shown.

LIST OF REFERENCE CHARACTERS

1 Active-liquid container
2 Atomizer below the active-liquid container 1
3 Aerosol dome above the active-liquid container 1
30 Baffle within the aerosol dome 3
31 Supply-air tube leading to the underside of the aerosol dome 3 via the cupola above the aerosol dome 3
32 Exhaust-air tube emerges from the top side of the aerosol dome 3
33 Exhalation tube, emerges from the side of the aerosol dome 3
34 Aerosol filter at the end of the exhalation tube 33
35 Supply-air valve at the inlet of the supply-air tube 31
36 Exhalation valve at the end of the exhalation tube 33
37 Mount of the baffle plate 30
38 Slit in the mount 37
4 Electronic control
5 User-command output
6 Carrier-liquid container between the atomizer 2 and the active-liquid container 1
71 Density sensor
72 Respiration detector
8 Mouthpiece

The invention claimed is:

1. A dosage inhaler, comprising:
   a carrier liquid container configured to contain a carrier liquid;
   an active liquid container configured to contain an active liquid having an active substance dissolved therein, wherein the active liquid container is configured to extend such that the active liquid container is partially immersed in the carrier liquid when the carrier liquid is contained in the carrier liquid container;
   an atomizer configured to intermittently generate and transmit oscillations through the carrier liquid to the active liquid to cause at least a portion of the active liquid to become an aerosol;
   an aerosol receiver providing a chamber configured to receive the aerosol;
   an exhaust-air tube in fluid communication with the aerosol receiver and configured to allow drops of the aerosol to flow therethrough;
   a baffle disposed in the aerosol receiver, wherein the baffle is hollow with an open end facing toward the active liquid container to receive the aerosol; and
   a hollow mount coupled to the baffle, wherein the hollow mount is positioned between the active liquid container and the exhaust-air tube, and the hollow mount includes a plurality of slits that permit fluid communication between the active liquid container and the exhaust-air tube.

2. The dosage inhaler of claim 1, wherein the active liquid container includes a frustoconical portion and a rounded tip.

3. The dosage inhaler of claim 2, wherein in operation of the dosage inhaler, the rounded tip of the active liquid container is immersed in the carrier liquid.

4. The dosage inhaler of claim 1, wherein the atomizer is positioned at a base of the carrier-liquid container.

5. The dosage inhaler of claim 1, further comprising an electronic control configured to control actuation of the atomizer such that generation of the aerosol within and below the aerosol receiver is separated in time from an inhalation of the aerosol.

6. The dosage inhaler of claim 1, further comprising a density sensor configured to measure a density of the aerosol within and below the aerosol receiver and to determine whether a predetermined volume of the aerosol in the aerosol receiver has been attained.

7. The dosage inhaler of claim 6, wherein the atomizer is configured to be activated for a predetermined period of time to generate aerosol, and if the density sensor determines that the predetermined volume of the aerosol in the aerosol receiver has not been attained, the atomizer is configured to be reactivated for an additional predetermined period of time.

8. The dosage inhaler of claim 1, further comprising:

an exhalation tube in fluid communication with the aerosol receiver; and a supply-air tube in fluid communication with the exhaust-air tube.

9. The dosage inhaler of claim 8, further comprising:

a filter in fluid communication with the exhalation tube.

10. The dosage inhaler of claim 8, further comprising:

an exhalation valve positioned at an outlet of the exhalation tube; and an air-supply valve positioned at an outlet of the supply-air tube, wherein in an exhalation stage in which the aerosol is generated, the exhalation valve is in an opened position and the air-supply valve is in a closed position, and wherein in an inhalation stage in which the drops of the aerosol are inhaled by the user, the exhalation valve is in a closed position and the air-supply valve is in an opened position.

11. The dosage inhaler of claim 1, further comprising a user-command output configured to instruct the user on how to breathe to achieve proper dosing, wherein the user-command output is configured to output at least a user-command that instructs the user to inhale and a user-command that instructs the user to exhale.

12. The dosage inhaler of claim 11, wherein the user-command output is further configured to output a user-command that instructs the user to wait in between the user-command that instructs the user to inhale and a subsequent user-command that instructs the user to exhale.

13. The dosage inhaler of claim 11, wherein the user-command output is configured to instruct the user on how to breathe to achieve proper dosing via sounds, symbols on a display, text on a display, speech, optical display elements or a combination thereof.

14. The dosage inhaler of claim 1, further comprising an inhalation piece connected to the exhaust-air tube and configured to assist the user in inhaling drops of the aerosol, wherein the inhalation piece is selected from the group consisting of a mouthpiece, a nose piece, and a face mask.

15. The dosage inhaler of claim 1, wherein the active liquid is contained in the active liquid container.

16. A method for using a dosage inhaler to administer an active substance, the method comprising:

filling at least a portion of a carrier liquid container with a carrier liquid;

filling at least a portion of an active liquid container with an active liquid having an active substance dissolved therein;

immersing at least a portion of the active liquid container in the carrier liquid;

activating an atomizer for a predetermined period of time to generate and transmit oscillations through the carrier liquid to the active liquid to cause at least a portion of the active liquid to become an aerosol; and introducing the aerosol into an open end of a hollow baffle disposed in a chamber provided by an aerosol receiver, the open end of the baffle facing toward the active liquid container; and causing aerosol within the open end of the baffle to flow from the baffle and through a plurality of slits in a hollow mount coupled to the baffle.

17. The method of claim 16, further comprising:

measuring, via a density sensor, a density of the aerosol within and below the aerosol receiver to determine whether a predetermined volume of the aerosol in the aerosol receiver has been attained; and if the predetermined volume of the aerosol in the aerosol receiver has not been attained, repeating the step of activating the atomizer until the predetermined volume of the aerosol in the aerosol receiver has been attained.

18. The method of claim 16, further comprising controlling actuation of the atomizer via an electronic control such that generation of the aerosol within and below the aerosol receiver is separated in time from an inhalation of the aerosol.

19. The method of claim 16, further comprising:

outputting an exhalation command via a user-command output to instruct a user to exhale; and outputting an inhalation command via the user-command output to instruct a user to inhale, wherein the user-command output outputs the exhalation command and the inhalation command via sounds, symbols on a display, text on a display, speech, optical display elements or a combination thereof.

20. The method of claim 19, further comprising:

measuring, via a density sensor, a density of the aerosol within and below the aerosol receiver to determine whether a predetermined volume of the aerosol in the aerosol receiver has been attained, wherein the inhalation command is only output after the density sensor determines that the predetermined volume of the aerosol in the aerosol receiver has been attained.

21. The method of claim 19, further comprising:

outputting a subsequent exhalation command via the user-command output to instruct the user to exhale;

activating the atomizer for a subsequent predetermined period of time;

outputting a subsequent inhalation command via the user-command output to instruct the user to inhale.

* * * * *

UNITED STATES PATENT AND TRADEMARK OFFICE
CERTIFICATE OF CORRECTION

PATENT NO. : 10,806,869 B2
APPLICATION NO. : 14/876394
DATED : October 20, 2020
INVENTOR(S) : Kern Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 913 days.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*